United States Patent [19]
Kaabi et al.

[11] Patent Number: 5,553,485
[45] Date of Patent: Sep. 10, 1996

[54] APPARATUS FOR MONITORING REHYDRATION KINETICS OF DEHYDRATED PRODUCTS

[75] Inventors: Carine Kaabi, Lausanne; Pierre Lambelet; Yvan Rossier, both of Saint Legier; Alfred Seiler, Lausanne, all of Switzerland

[73] Assignee: Nestec S.A., Vevey, Switzerland

[21] Appl. No.: 195,534

[22] Filed: Feb. 14, 1994

[30] Foreign Application Priority Data

Mar. 11, 1993 [EP] European Pat. Off. ............... 93103928

[51] Int. Cl.⁶ .................................................. G01N 5/02
[52] U.S. Cl. .................................................. 73/73; 177/50
[58] Field of Search ............................. 73/76, 73; 177/50

[56] References Cited

U.S. PATENT DOCUMENTS 3,665,755  5/1972  Krostewitz .................................. 73/73

FOREIGN PATENT DOCUMENTS 3123655  1/1983  Germany .................................. 73/76
3922380  of 1990  Germany .
0089747  7/1980  Japan .................................. 73/76
0216358  4/1968  U.S.S.R. .................................. 73/76
0862073  9/1981  U.S.S.R. .................................. 73/73
1566269  5/1990  U.S.S.R. .................................. 73/73

OTHER PUBLICATIONS

Derwent Publications Ltd., London, GB, Soviet Inventions Illustrated, Section E1, Week K42, Abstract Acc. No. 83–794107/42 of Soviet patent Su–A–983 514 (1983) (only abstract considered).

Primary Examiner—Diego F. F. Gutierrez
Attorney, Agent, or Firm—Vogt & O'Donnell, LLP

[57] ABSTRACT

An apparatus assembly for monitoring the rehydration kinetics of dehydrated products has an enclosure formed by a cage for holding the products and by a cover for the cage surmounted by a hollowed rod. In use, the enclosure is connected via the rod with the pan of a balance so that it is suspended over the balance pan. The lattice-work of the side portion of the cage is configured so that when the cage is immersed in water, the lattice-work allows water to pass therethrough but prevents air from escaping from the cage through the lattice-work.

12 Claims, 3 Drawing Sheets

APPARATUS FOR MONITORING REHYDRATION KINETICS OF DEHYDRATED PRODUCTS

BACKGROUND OF THE INVENTION

The present invention relates to means for monitoring the rehydration kinetics of dehydrated products, particularly water-insoluble dehydrated products.

Hitherto, the following procedure has been adopted to determine the rehydration of dehydrated products, for example pastas. The pastas are soaked in water under normal reconstitution conditions, i.e., at a water temperature of the order of 80° C., and are then weighed at regular time intervals after draining. This procedure is not at all practical because it necessitates the almost permanent presence of an operator and gives unreliable and non-reproducible results because the draining step can lead to the unwanted presence of water and depends upon the method of operation of each user.

SUMMARY OF THE INVENTION

The problem addressed by the present invention was to provide a method and an apparatus for continuously monitoring the rehydration kinetics of dried products which would be more universal and more reliable and which would provide for automatic monitoring without requiring the permanent presence of an operator.

The present invention provides an apparatus for determining the rehydration kinetics of a dehydrated product which includes suspension means fixed to the pan of a balance and an enclosure for holding the dehydrated products comprising a cage wherein the cage openings allow the water to pass through but keep the air inside and comprising a cover for the cage surmounted by a hollow rod designed to engage with the suspension means.

In the process according to the invention, the dehydrated products are immersed in water at the desired temperature and the variation in the force applied to the pan of the balance of the apparatus assembly by the combination of the product and the water of rehydration accommodated in the cage and enclosure of the apparatus assembly is monitored as a function of time.

DETAILED DESCRIPTION OF THE INVENTION

In accordance with the process of the present invention, the variation in force takes into account the Archimedean pressure applied to the product in accordance with the following relation:

$$\Delta F = \rho(\Delta V_o - \Delta V)$$

where
  $\Delta F$ is the variation in the force measured by the balance,
  $\rho$ is the specific gravity of the water,
  $\Delta V_o$ is the variation in the volume of water in the enclosure accommodating the product to be rehydrated and
  $\Delta V$ is the variation in volume of the sample.

The advantage of this method lies in the fact that it is sufficient to immerse the sample in water and to connect it to a weighing system to be able to monitor the variation in force as a function of time without any other manipulation.

The insoluble dehydrated products suitable for analysis by the method according to the invention are vegetables, fruits, meat and also pastas and rice, both conventionally dried and freeze-dried.

The advantage of knowing the rehydration kinetics of dried products arises out of the fact that it is important to know how much time is required for completely rehydrating carrots, for example, where they are part of a mixture for dehydrated soup which is required to be ready after a time t. Now, it is obvious that the dehydrated carrots must lend themselves to reconstitution in less than the time t so that the product obtained has the appropriate texture.

In addition, when the dehydrated product, for example a pasta, is reconstituted by the consumer, a temperature near the boiling point of water is applied. Accordingly, provision has to be made for measurement of the rehydration kinetics at temperatures close to those encountered under actual reconstitution conditions. The method according to the invention is carried out at a temperature of 20° to 90° C.

The rehydration time is also determined by the temperature. The higher the temperature, the shorter the rehydration time. The rehydration time is generally between 30 seconds and 24 hours and preferably between 5 and 30 minutes.

In carrying out the process and utilizing an apparatus of the present invention, during the measurement, the holding system containing the dehydrated product is immersed in such a way that the water enters through the openings in the cage and impregnates the product. The variation in the force applied to the suspension means is then monitored as a function of time through the connection of the balance to a data acquisition system.

In the apparatus of the present invention, the suspension means normally consists of a bracket. To prevent the sample from rising, a grill is provided inside the cover of the cage. When the holding system is immersed in the water, it is important that the air displaced into the cage escapes therefrom. To this end, a closure cone fixed to a spring is provided inside the hollowed rod. During the immersion process, the hollowed rod is kept open to remove the air and is then reclosed for the entire duration of the measurement.

In addition, the arrangement according to the invention comprises a system for controlling the rehydration temperature so that it is able to operate at the actual temperatures used by the consumer.

Instead of monitoring the variation in the force applied for the suspension means, the variation in the weight of the container accommodating the water used for rehydration may also be monitored. To this end, the container is placed on the pan of the balance and the suspension means of the boat are kept separate from the balance. In this case, the relation becomes:

$$\Delta F = \rho(\Delta V - \Delta V_o).$$

The invention is described in more detail in the following with reference to the accompanying drawings.

DETAILED DESCRIPTION OF THE DRAWINGS

Figure 1:
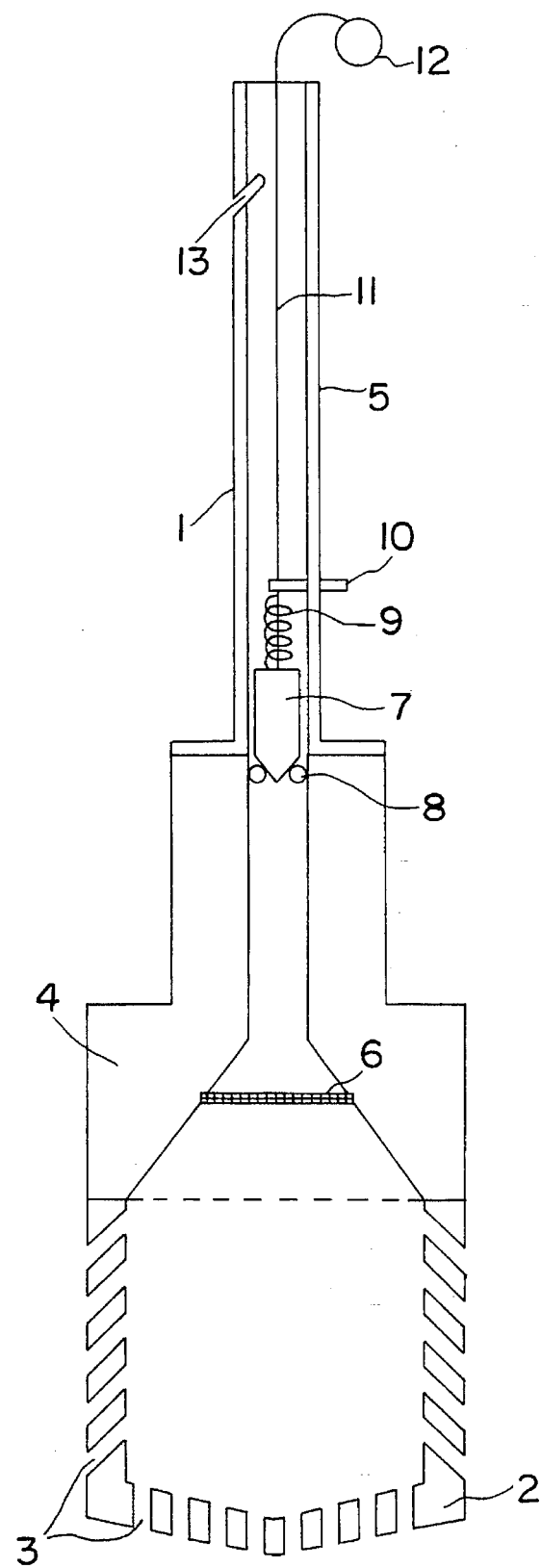
FIG. 1 is a section through the holding system according to the invention.

The holding system (1) (FIG. 1) comprises a cage (2) which has a base portion and has a side portion which extends from the base portion to an edge which defines a cage opening which opposes the base portion and in which the product to be rehydrated is placed. The lattice-work of the cage (2) defines a plurality of openings (3) for circulation of the water. The openings defined by the lattice-work of the side portion of the cage are directed in such a way as to prevent air from escaping from that portion of the enclosure accommodating the sample. The number and shape of the openings are not critical. The base portion outer surface of the cage is conical to promote the ascent of the bubbles formed at the bottom of the enclosure at high temperatures.

Figure 2:
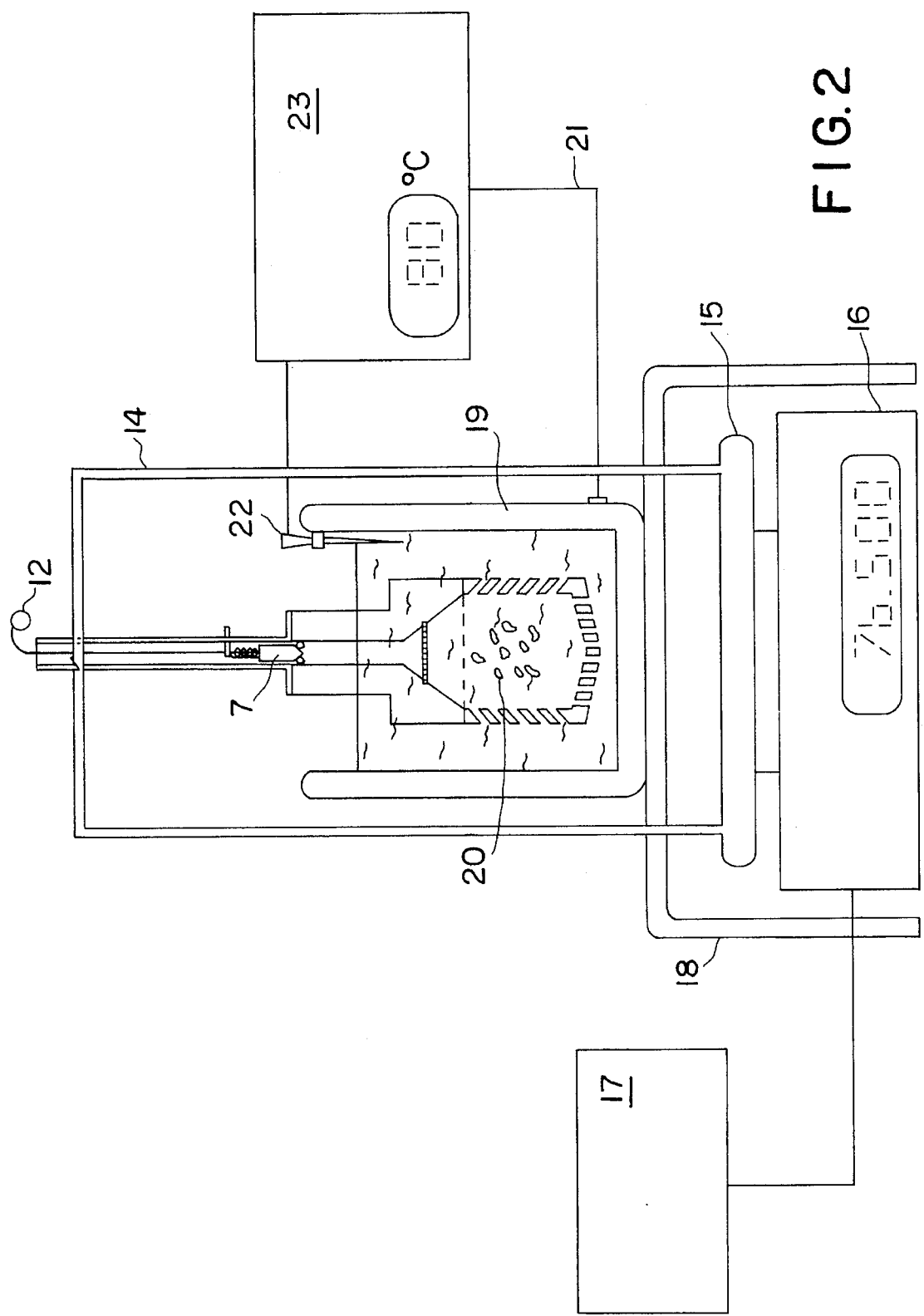
FIG. 2 diagrammatically illustrates the arrangement according to the invention.

The system further comprises a cover (4) surmounted by a hollowed rod (5). The cover (4), as illustrated, has a solid cover portion which surrounds a cover portion surface which defines a hole opening through the cover portion, and the hollowed rod (5) extends from the cover portion so that the hollow of the hollowed rod (5) extends from the cover portion hole and so that when the cover covers the cage opening which opposes the case base portion, the cover portion hole opening opposes the cage base portion, and the hollowed rod extends in a direction away from the cage base portion. The cover is fixed to the cage by a bayonet system. A grill (6) is provided in a space defined by a surface inside the cover to prevent the product to be analyzed from ascending. The interior of the suspension rod comprises a closure cone (7) which bears against a sealing ring (8) for seating the closure cone member (7). The closure cone is connected to a spring (9) which bears against a stop (10). A metal wire (11) connects the cone (7) to a ring (12), enabling the operator to open the system to allow the air to escape. A slot (13) is provided to suspend the system from a bracket (14) (FIG. 2) fixed to the pan (15) of a balance (16). The balance is connected to a data acquisition system (17).

The container (19) accommodating the water in which the holding system (1) is immersed is placed on a support (18) independent of the balance. The container (19) comprises a heating jacket connected at (21) to the temperature control system (23). The system (23) is under the control of a temperature probe (22).

The product (20) to be rehydrated is placed in the cage (2) which is reclosed, the system (1) is immersed in the water and is then suspended from the bracket (14). At this moment, the closure (7) is raised to allow the air to escape and is then reclosed. The balance then indicates (t=0) the initial force applied to the bracket.

The variation in that force is then monitored as a function of time.

Figure 3:
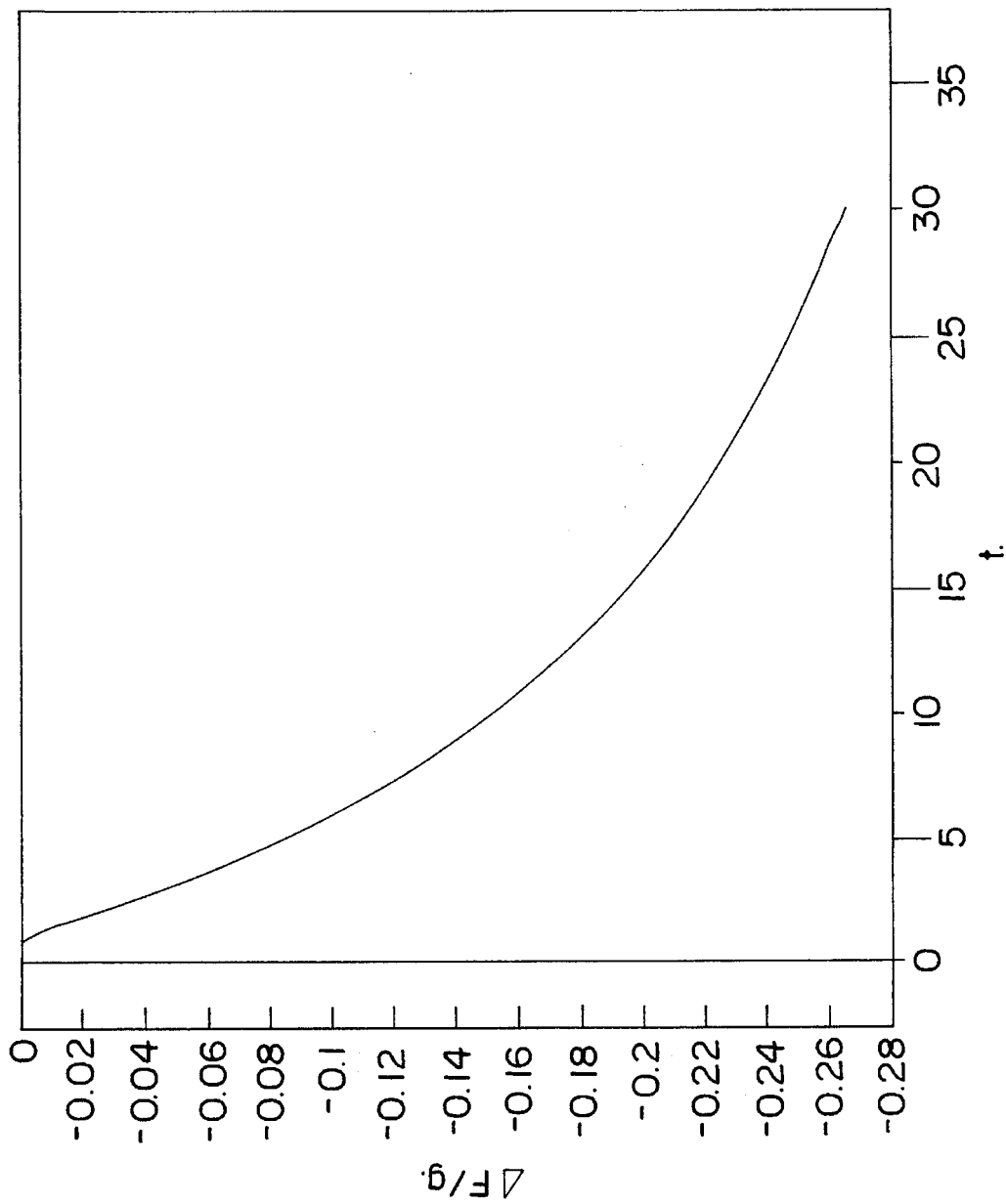
FIG. 3 is a graph of the rehydration kinetics for carrots.

The invention is illustrated by the following Example in conjunction with FIG. 3 which shows the rehydration kinetics of carrots.

EXAMPLE

Using the system described above, 10 g of carrots are immersed in tapwater at 22° C. The force F(t) applied to the balance by the bracket is recorded for 30 minutes. The initial force F(t=0) is subtracted from that force at each instant so that the value $\Delta F(t)$ is obtained. This value is then corrected by subtracting the corresponding value $\Delta F'(t)$ observed under the same conditions, but in the absence of a sample (blank), at each instant. Finally, the corrected value of $\Delta F(t)$ is standardized in relation to the weight of the sample. The curve shown in FIG. 3 is thus obtained. The fact that the signal observed decreases with time is due to the swelling of the carrots during their rehydration ($\Delta V > \Delta Vo$).

We claim:

1. An apparatus assembly for monitoring rehydration characteristics of dehydrated products comprising:
   a cage and a cover which is movable for, together with the cage, forming a cage and cover enclosure wherein:
      the cage has a lattice-work base portion and has a lattice-work side portion which extends from the base portion to an edge which defines a cage opening which opposes the base portion and wherein the side portion lattice-work is configured so that when the cage is immersed in water so that the cage opening is positioned vertically above the base portion, the side portion lattice-work allows water to pass therethrough but prevents air from escaping from the cage therethrough; and
      the cover has a solid cover portion which surrounds a cover portion surface which defines a hole opening through the cover portion and has a hollowed rod portion which extends from the cover portion so that the hollow of the hollowed rod portion extends the cover portion hole opening and wherein the cover portion and hollowed rod portion are configured and positioned so that when the cover covers the cage opening to form the enclosure, the cover portion hole opening opposes the cage base portion and the hollowed rod portion extends in a direction away from the cage base portion;
   a balance having a balance pan positioned beneath the enclosure; and
   means for connecting the balance pan and the hollowed rod portion for, when the cover covers the cage opening, suspending the cage and cover enclosure above the balance pan so that the cover is disposed vertically above the cage base portion.

2. An apparatus assembly according to claim 1 further comprising a movable closure member positioned in the hollow of the hollowed rod portion for movement in the hollow of the rod for controlling escape of air.

3. An apparatus assembly according to claim 2 further comprising a sealing ring which is positioned to extend within the hollow of the hollowed rod portion for seating the closure member for controlling escape of air.

4. An apparatus assembly according to claim 3 further comprising a spring and a stop positioned in the hollow of the hollowed rod so that the spring is positioned between the stop and the closure member and bears upon the closure member for seating the closure member in the sealing ring.

5. An apparatus assembly according to claim 1 or 2 wherein the cover has a surface which defines a cover space and further comprises a grill positioned within the space so that when the cover covers the cage opening, the grill is positioned between the cage opening and the cover portion hole opening so that upon immersion of the cage in water so that the cover is disposed vertically above the cage base portion, dehydrated product in the cage is prevented from passing through the cover hole opening into the hollow of the rod.

6. An apparatus assembly according to claim 5 wherein the cage base portion has an outer surface having a conical shape which extends from the cage side portion to a cone apex.

7. An apparatus assembly according to claim 1 or 2 wherein the cage base portion has an outer surface having a conical shape which extends from the cage side portion to a cone apex.

8. An apparatus assembly according to claim 1 further comprising a data acquisition system connected with the balance for monitoring variation in force applied to the balance pan as a function of time.

9. An apparatus assembly according to claim 1 further comprising a container for containing water and for containing the cage and cover enclosure so that the cage is immersible in the water and further comprising a support for supporting the container independent of the balance.

10. An apparatus assembly according to claim 9 further comprising a heating system for heating water in the container.

11. An apparatus assembly according to claim 9 wherein the container is a jacketed container for heating water contained in the container.

12. An apparatus assembly according to claim 9 further comprising a system for controlling the heating system.

* * * * *